United States Patent [19]
Peterson et al.

[11] Patent Number: 5,435,399
[45] Date of Patent: Jul. 25, 1995

[54] SOIL SAMPLER

[75] Inventors: Gary G. Peterson; Jacob N. Gust, both of Fargo, N. Dak.; Virgil R. Mahlum, Lake Park, Minn.; Michael W. Smette, Fargo, N. Dak.

[73] Assignee: Concord, Inc., Fargo, N. Dak.

[21] Appl. No.: 271,064

[22] Filed: Jul. 5, 1994

[51] Int. Cl.[6] ............................................. E21B 49/02
[52] U.S. Cl. ........................................ 175/20; 175/55; 175/58; 175/135; 175/203; 73/864.31
[58] Field of Search .................. 175/19, 20, 50, 55, 175/58, 135, 203; 73/864.31, 864.45

[56] References Cited

U.S. PATENT DOCUMENTS

| Re. 29,087 | 12/1976 | Larson | 73/864.31 |
|---|---|---|---|
| 2,084,686 | 6/1937 | Howard | 73/864.45 X |
| 2,287,059 | 6/1942 | Platts et al. | 255/1.4 |
| 2,643,858 | 6/1953 | Hardman | 73/864.45 X |
| 2,667,752 | 2/1954 | Moseley | 61/73 |
| 3,084,553 | 4/1963 | Cullinan et al. | 73/864.31 |
| 3,224,512 | 7/1963 | Alexander | 173/19 |
| 3,450,073 | 6/1969 | Baker | 111/6 |
| 3,464,504 | 9/1969 | Stange | 73/864.45 X |
| 3,507,338 | 4/1970 | McWaters et al. | 173/28 |
| 3,593,809 | 7/1971 | Derry | 175/51 |
| 3,710,876 | 1/1973 | Christensen | 173/43 |
| 3,977,479 | 8/1976 | Sainsbury | 175/58 |
| 4,029,158 | 6/1977 | Gerrish | 405/232 X |
| 4,081,040 | 3/1978 | Henson | 175/58 |
| 4,112,692 | 9/1978 | Anderson et al. | 405/271 |
| 4,166,508 | 9/1979 | Van Den Berg | 175/20 |
| 4,284,150 | 8/1981 | Davis | 175/20 X |
| 4,316,393 | 2/1982 | Philipenko | 73/864.45 |
| 4,332,301 | 6/1982 | Jonell | 175/50 |
| 4,333,541 | 6/1982 | Doty | 175/162 |
| 4,685,339 | 8/1987 | Philpenko | 73/864.45 |
| 4,732,227 | 3/1988 | Wolf et al. | 175/170 |
| 4,836,294 | 6/1989 | Bencriscutto | 172/22 |
| 5,058,688 | 10/1991 | Scott et al. | 175/20 |
| 5,076,372 | 12/1991 | Hellbusch | |
| 5,090,486 | 2/1992 | Jones | 173/26 |

OTHER PUBLICATIONS

Geoprobe Systems Equipment and Tools Catalog 1992, cover page.
Agronomy Journal, vol. 85, No. 1; Jan.–Feb. 1993, pp. 179–181.

Primary Examiner—Roger J. Schoeppel
Attorney, Agent, or Firm—Kinney & Lange

[57] ABSTRACT

A soil sampler for taking soil samples at multiple locations around a vehicle is disclosed. The soil sampler has a probe for withdrawing soil samples from the ground. The probe is suspended on a support structure or boom assembly which can move the probe to multiple withdrawal locations around a vehicle. The soil sampler has a percussion-type vibrator to aid in inserting the probe into the ground. The vibrator assembly operates automatically off of a hydraulic line used to lower the boom assembly, such that the vibrator normally operates only when the probe is encountering significant resistance to being pressed into the ground. The support structure is raisable to allow an operator within the vehicle to collect multiple soil samples without leaving the vehicle.

25 Claims, 10 Drawing Sheets

SOIL SAMPLER

BACKGROUND OF THE INVENTION

This invention is directed to soil sampling, and more particularly to a method and apparatus for sampling soil at multiple locations around a vehicle.

Soil sampling has been done in the past for various agricultural purposes. Soil samples are taken from the top few feet of ground where plants and their roots grow. The samples are analyzed to determine the relevant chemical properties of the soil, moisture content, etc. Sampling results are then used to determine an agricultural strategy which may include such determinations as the type and spacing of crops most suitable for the soil, the proper type and amount of fertilizer, the proper type and amount of herbicide, etc.

As soil sample results have become more and more valuable in determining an effective agricultural strategy, it has been recognized that single samples do not always provide accurate results. Occasionally very localized soil content anomalies will cause the sample taken not to be indicative of the area of the field that the sample represents. Accordingly, it is now recommended that multiple soil samples be taken from a star-shaped pattern, from locations on a circle of a diameter not less than twelve (12) feet. Such a star pattern ensures significant spacing between multiple soil samples, so that very localized soil anomalies can be avoided. Averaging techniques can then be used to better determine a proper agricultural strategy for that section of the plot.

Through star pattern sampling techniques, accurate soil characteristics can be determined for fairly large sampling spacing. For example, one star pattern may accurately reflect soil conditions over a 2 to 4 acres span. Sizable plots will obviously require numerous star patterns to determined broad-based changes in soil content. Accurate averaged results from these numerous star patterns can then be further manipulated to provide an agricultural strategy which takes into account variations in soil conditions across a large plot. For instance, global satellite positioning can be utilized in conjunction with soil sample results to automatically alter the amount and type of fertilizer spread during runs across the field by a single unit. As agricultural strategy becomes more and more sophisticated, the importance of soil sampling is becoming more and more significant.

Previous soil samplers have taken samples from a single location off of the vehicle to which the sampler is mounted. For instance, U.S. Pat. No. 4,685,339 to Philipenko and owned by the assignee of the present invention, discloses a soil sampler which is mounted on a vehicle such as a pickup truck. The Philipenko soil sampling probe moves vertically to take a sample, but does not otherwise move with respect to the pickup truck. To take samples from multiple locations, the pickup truck must be moved.

SUMMARY OF THE INVENTION

The present invention is a method and apparatus for taking soil samples from multiple locations around a vehicle. A soil sampler has a probe which is pressed into the ground. Withdrawal of the probe from the ground ejects a sample into a sample collection receptacle. The probe is carried by a movable support structure or boom assembly. The base of the boom assembly can be attached into a bed of a pickup truck or on a trailer. The boom assembly moves through two hydraulically powered features: a rotation motor which can rotate the boom assembly through about 280° of rotation; and a cylinder which can raise and lower the boom assembly (and the probe attached thereto). The boom assembly also carries a second hydraulically powered motor which energizes a percussion vibrator which can hammer the probe into the ground. The vibrator is particularly useful for pressing the probe into the ground at locations spaced from the vehicle wheel base. The vibrator motor is automatically activated by a pressure sensitive switch on the hydraulic cylinder, such that the vibrator selectively operates when the boom assembly encounters significant pressure in pressing the probe into the ground. The boom assembly can also raise the probe to the driver's vehicle window, such that the sample collection receptacle can be removed by an operator without leaving the cab of the vehicle. The sample collection receptacle can house numerous samples, such as from the four or five locations of the star patterns described earlier.

While the above-identified drawing figures set forth alternative embodiments, other embodiments of the present invention are also contemplated, as noted in the discussion. In all cases, this disclosure presents illustrated embodiments of the present invention by way of representation and not limitation. Numerous other modifications and embodiments can be devised by those skilled in the art which fall within the scope and spirit of the principles of this invention.

DETAILED DESCRIPTION OF THE PREFERRED EMBODIMENTS

Figure 1:
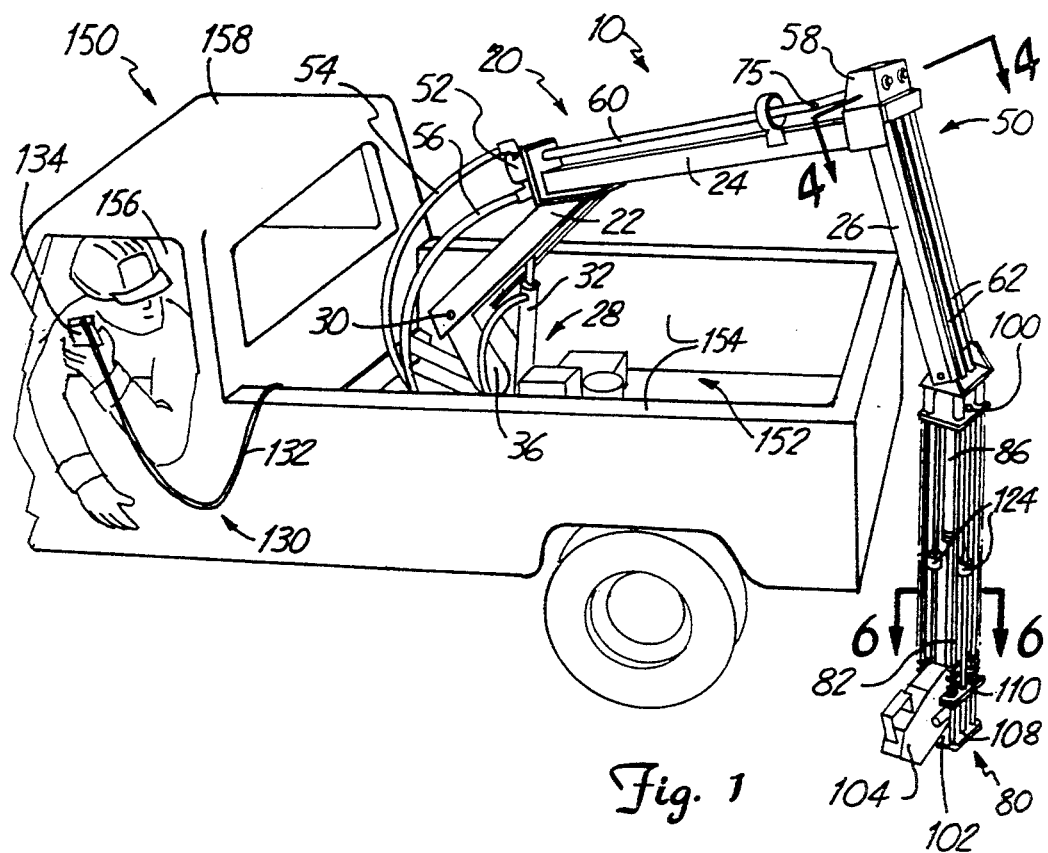
FIG. 1 is a side perspective view of the soil sampler of the present invention mounted in the bed of a pickup truck.
Figure 2:
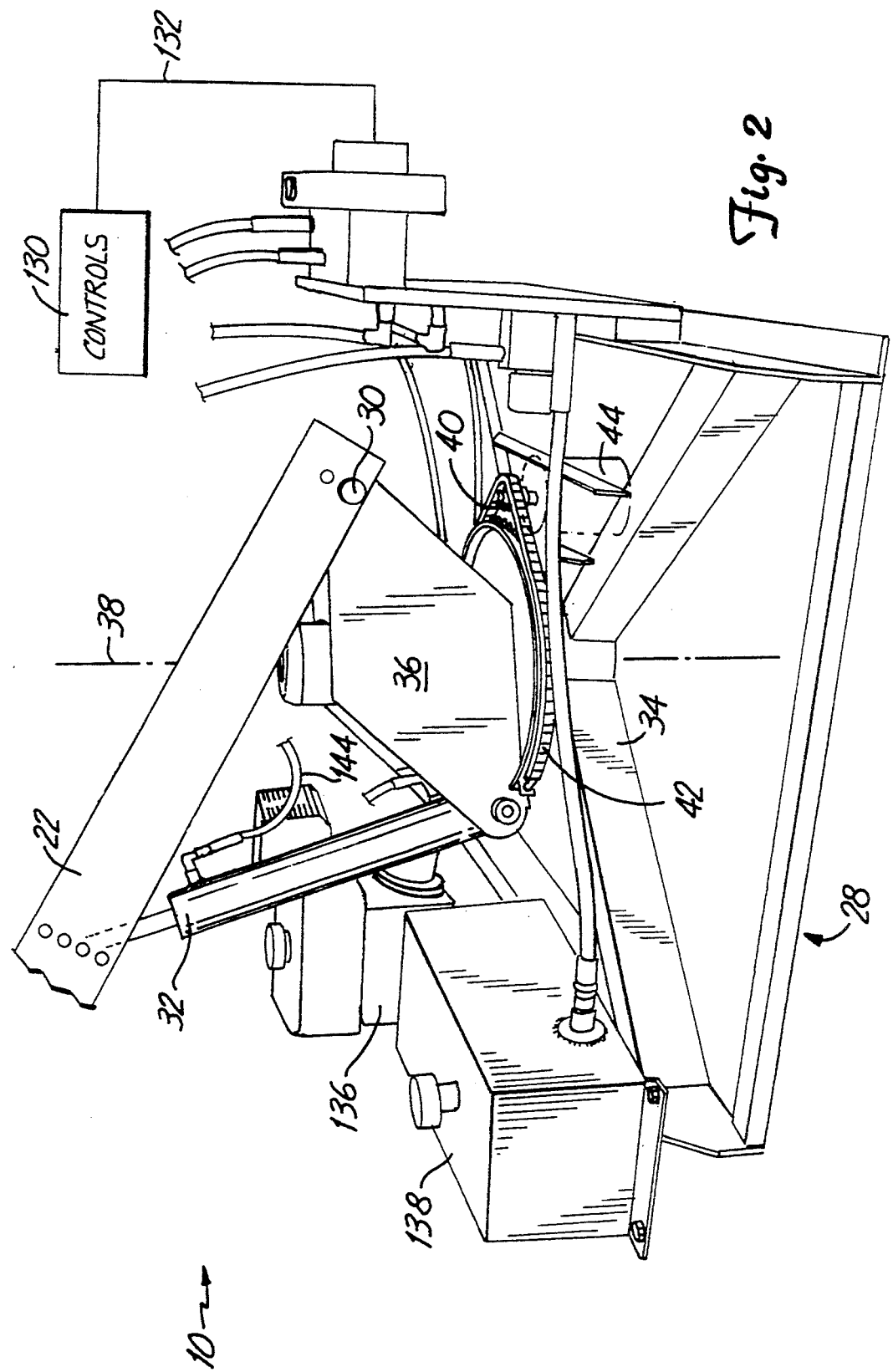
FIG. 2 is a perspective view of the base section of the soil sampler.
Figure 3:
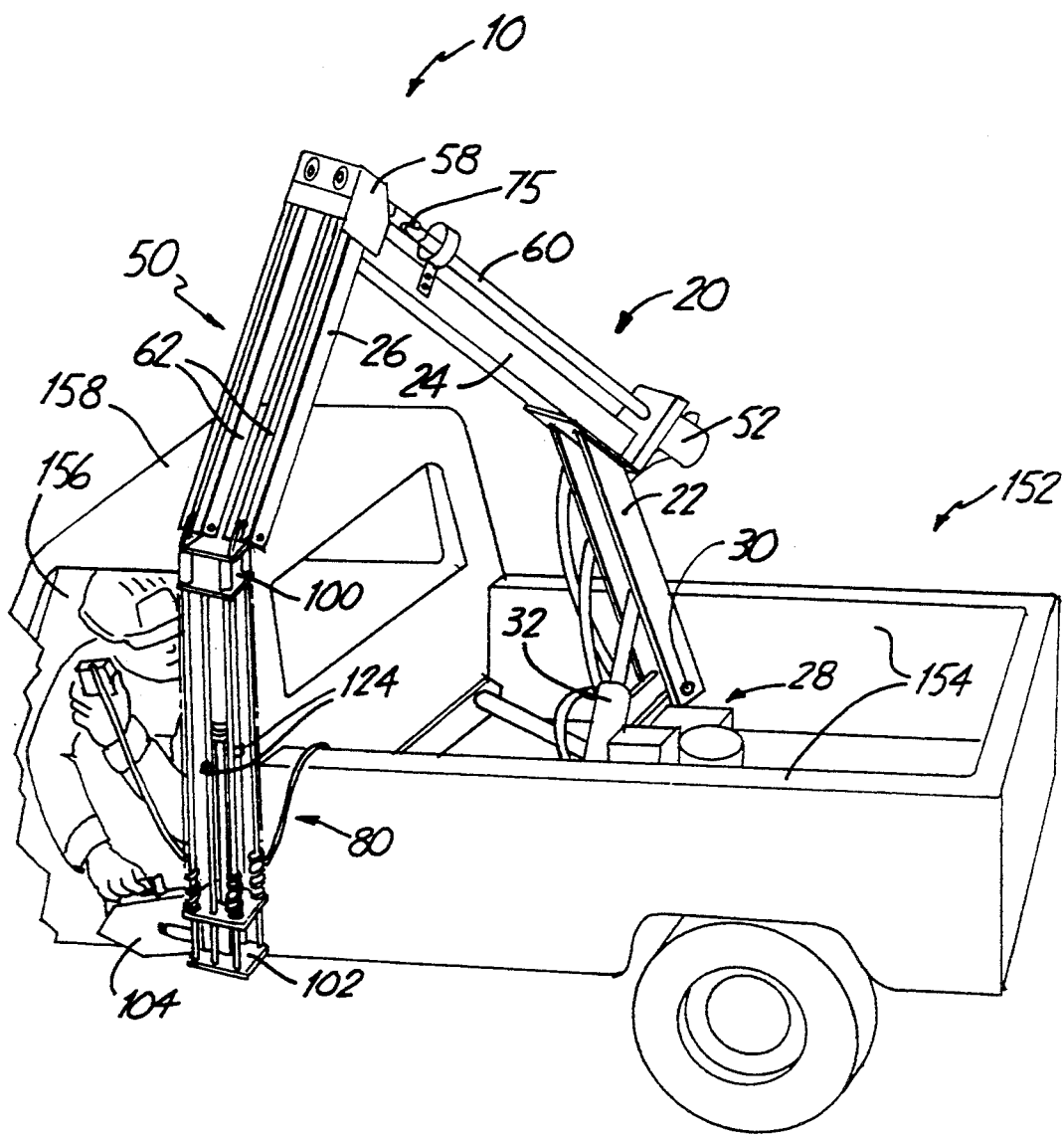
FIG. 3 is a side perspective view of the soil sampler in position for the pickup truck operator to remove the sample collection receptacle from the probe.

As shown in FIGS. 1-3, soil sampler 10 of the present invention includes boom assembly 20, vibrator assembly 50, probe assembly 80 and control panel 130.

Boom assembly 20 includes three (3) beams 22, 24, 26 supported on base 28. Base 28 of soil sampler 10 is shown attached in the bed 152 of a pickup truck 150. Base beam 22 is pivotally attached to base 28 at pivot point 30 and supported by hydraulic cylinder 32. Intermediate beam 24 rigidly connects base beam 22 to outer beam 26. Extension of hydraulic cylinder 32 raises the entire boom assembly 20 through rotation about pivot point 30, and shortening hydraulic cylinder 32 lowers boom assembly 20. This rotation of boom assembly 20 about pivot point 30 provides a first degree of freedom of the boom assembly system for placing the probe assembly 80 in the proper position. As will be described below, hydraulic cylinder 32 may be shortened and boom assembly 20 lowered past contact of probe assembly 80 with the ground, so as to force probe 82 into the ground.

As shown in FIG. 2, base 28 includes a lower anchoring portion 34 which may be securely anchored into bed 152 of pick-up truck 150. An upper rotating portion 36 of base 28 rides on bearings to allow rotation about axis 38. Gear 40 engages in chain 42, and chain 42 extends around and is secured to upper rotating portion 36. A hydraulically driven motor 44 rotates gear 40, which in turn rotates upper rotating portion 36. Because boom assembly 20 is attached to upper rotating portion 36, energizing of motor 44 rotates the entire boom assembly 20 about axis 38, through the length of travel of chain 42. This rotation of boom assembly 20 about axis 38 provides a second degree of freedom of the boom assembly system.

Upper rotating portion 36 can preferably be rotated through a 288° arc about axis 38. Cylinder 32 and rotation motor 44 thus allow probe assembly 80 to be raised or lowered anywhere on this 288° arc, allowing probe assembly 80 to take samples in a star-shaped collection pattern about axis 38. As shown in FIG. 3, a 288° arc also allows sample collection receptacle 104 to be raised to an access location for an operator inside the cab 158 of the vehicle. Eaton Corp. of Cleveland, Ohio provides a #101-1007, 17.9 cubic inch hydraulic motor which is suitable for rotation motor 44. Workers skilled in the art will appreciate that more or less rotation, including continuous rotation through a 360° circle, may be beneficial to their particular circumstances.

Workers skilled in the art will recognize that many other types of boom assemblies would also be suitable for this application, provided they effective support the probe for movement to multiple locations. Three rigidly connected beams 22, 24, and 26 are preferred for raising boom assembly 20 over the walls 154 of the pickup truck bed 152 and for adequately positioning the various components of soil sampler 10, but other types of boom assemblies may also be suitable. For instance, while boom assembly 20 as described only includes two degrees of freedom (raising/lowering and rotation), workers skilled in the art will appreciate that a third degree of freedom, allowing movement of probe assembly 80 toward and away from the pickup truck 150, may be beneficial. This could easily be accomplished by adding a second hydraulic cylinder between beams, by making one or more of the beams extendable, or by other ways known in the art. While the boom assembly shown only allows probe assembly 80 to be positioned along an arc centering on rotation axis 38, a third degree of freedom would allow probe assembly 80 to be placed anywhere between the pickup truck 150 and the external reach of boom assembly 20.

Figure 4:
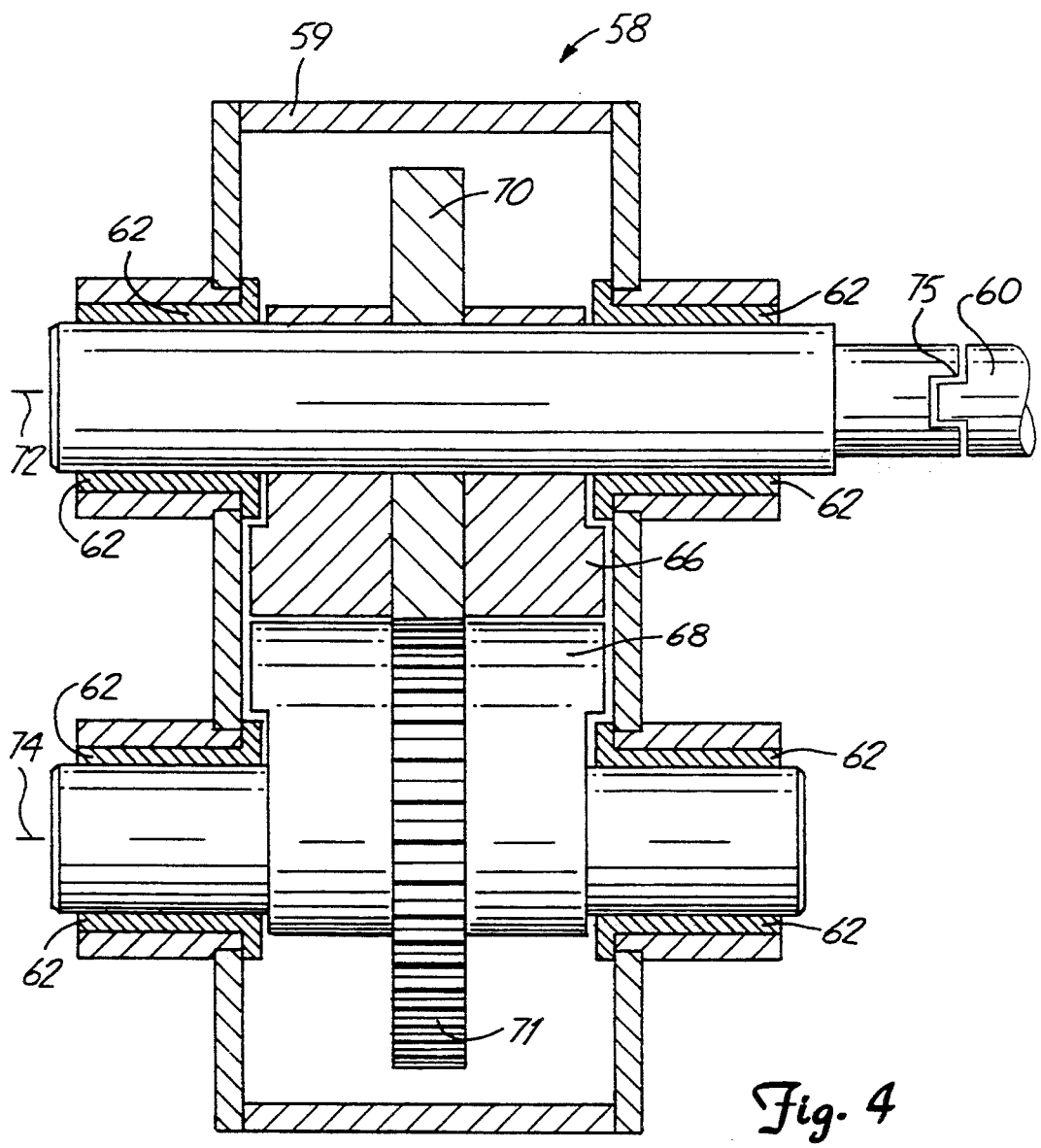
FIG. 4 is a broken out cross-sectional view of the vibrator weights taken along line 4—4 of FIG. 1.
Figure 5:
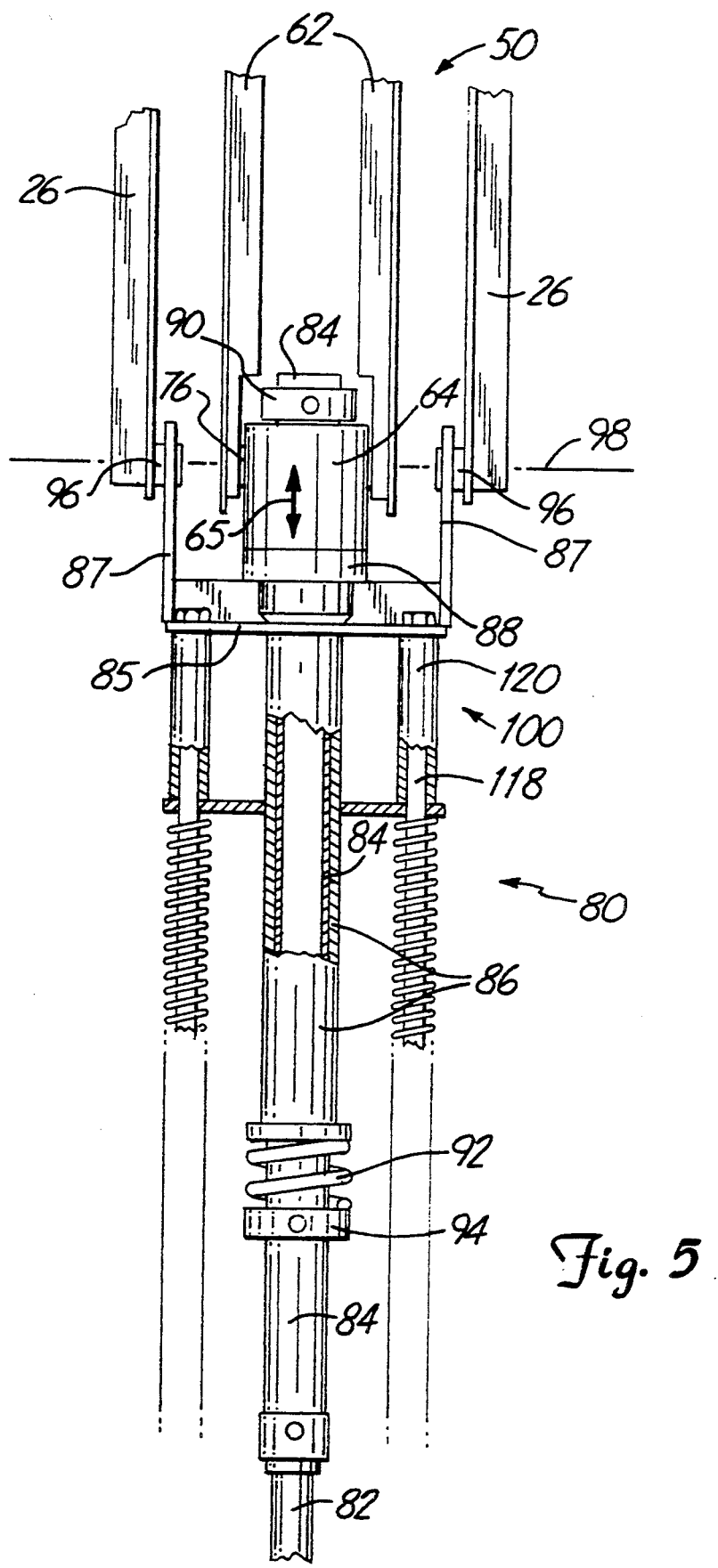
FIG. 5 is a side elevational view of the hammer and probe stem section of the soil sampler, shown in partial cross-section.

A preferred vibrator assembly 50 and its components are best shown in FIGS. 1, 4 and 5. As shown in FIG. 1, preferred vibrator assembly 50 includes hydraulically powered vibrator motor 52 mounted along the joint between base beam 22 and intermediate beam 24. Gresen Manufacturing Co. of Minneapolis, Minn. provides a MGG 2002 0.450 cubic inch motor which is suitable for vibrator motor 52. Vibrator motor 52 is shown with hydraulic feed line 54 and hydraulic return line 56 attached. Vibration unit 58 is shown mounted along the joint between intermediate beam 24 and outer beam 26, and is powered from vibrator motor 52 via drive shaft 60. Vibration unit 58 causes vibration arms 62 to reciprocate.

As shown in FIG. 4, vibration unit 58 includes housing 59 around two eccentric weights 66, 68. Drive shaft 60 rotates eccentric weight 66 about axis 72. Through gears 70, 71 eccentric weight 68 is rotated in the opposite direction about axis 74. Vibration unit 58 is rigidly attached to vibration arms 62. Vibration arms 62 are supported by but not rigidly attached to housing 59, such that vibration is substantially transmitted only to vibration arms 62 and not to housing 59 and the rest of boom assembly 20.

In the horizontal direction, the vibration caused by rotation of eccentric weight 66 offsets the vibration caused by eccentric weight 68. In the direction of outer beam 26 and vibration arms 62 (i.e., normal to the axis 72, 74), the vibration caused by both eccentric weights 66, 68 is additive. Vibration unit 58 is contained by but not attached to boom assembly 20, allowing essentially vertical motion of vibration unit 58 and attached arms 62.

A preferred vibrator assembly 50 uses drive shaft 60 to separate vibration unit 58 from motor 52, to lessen the harmful effects of such repeated vibration on motor 52. Drive shaft 60 contains U-joint 75 which significantly dampens the vibration from reaching motor 52. Workers skilled in the art will appreciate that widely varied alternative mounting arrangements and widely varied alternative vibrator assemblies may prove beneficial, so long as they transfer vibration to probe 82 to aid in inserting probe 82 into the ground.

The structure for transfering reciprocating motion from vibration arms 62 to probe 82 is best described with reference to FIG. 5. Hammer 64 is pivotally attached to vibration arms 62. Hammer 64 is preferably a tubular sleeve which rides on probe stem 84 between stroke fixing collar 90 and anvil 88. Upper guide assembly 100 includes platform 85, stem guide 86 and ears 87, and is pivotally attached to outer beam 26 by ears 87 and pins 96. Probe 82 is attached to probe stem 84, and probe stem 84 slides vertically within stem guide 86. Spring collar 94 is attached on the lower side of probe stem 84, anvil 88 is attached to probe stem 84 at an intermediate position (above stem guide 86 but below hammer 64), and stroke fixing collar 90 is attached on the upper side of probe stem 84. Compression spring 92 is carried on probe stem 84 between spring collar 94 and stem guide 86. Spring collar 94 butting up against compression spring 92 and the lower side of stem guide 86 limits upward sliding of probe stem 84. Anvil 88 butting up against the upper side of stem guide 86 limits downward sliding of probe stem 84. Spring collar 94 and stroke fixing collar 90 are preferably attached to probe stem 84 by a set screw, allowing adjustment of collar position and ease of assembly. Anvil 88 is preferably welded to probe stem 84.

The operation of the hammer structure shown in FIG. 5 is as follows. Compression spring 92 retains probe stem 84 in an extended position, unless probe 82 is being inserted into the ground. During insertion (i.e., lowering of outer beam 26), ground resistance tends to press probe 82 and probe stem 84 upward relative to upper guide assembly 100 and stem guide 86. When ground resistance is sufficient, the vibrator assembly 50 is energized. Energizing of vibrator motor 52 causes rotation of drive shaft 60, which in turn causes rotation of eccentric weights 66, 68, which in turn causes linear reciprocation of vibration arms 62. Reciprocation of vibration arms 62 moves hammer 64 vertically back and forth in direction 65. During each downstroke, hammer 64 slides on probe stem 84 until it strikes anvil 88, hammering probe stem 84 and probe 82 downward. The length of upstroke of hammer 64 is controlled by the positioning of stroke fixing collar 90 in conjunction with the dampening effect of compression spring 92. Reciprocation of vibration arms 62 thus causes hammer 64 to repeatedly hammer probe stem 84 downward into the ground.

As shown in FIG. 5, probe assembly 80 is attached to outer beam 26 by pins 96, such that probe assembly 80 can pivot about axis 98. A preferred probe assembly 80 pivots freely about axis 98, which is defined by pins 96. The pin connection allows probe assembly 80 to be repeatedly placed in an appropriate vertical orientation through gravity and make appropriate contact with the ground surface without regard to the orientation of truck 150 and boom assembly 20. The pin connection further allows probe assembly 80 to be folded into the pickup bed 152 when transporting soil sampler 10 between locations. To provide the same pivoting freedom, hammer 64 is attached to vibration arms 62 through pins 76 such that hammer 64 can also pivot about axis 98.

As shown in FIGS. 1 and 5–8 probe assembly 80 includes probe 82, upper guide assembly 100, lower guide assembly 102, and sample collection receptacle 104. Probe 82 is preferably as described in U.S. Pat. No. 4,685,339 to Philipenko, which is incorporated herein by reference. Workers skilled in the art will recognize that any sort of probe may be incorporated to better meet their purposes, so long as the probe takes a soil sample from the ground. When probe 82 is pressed into the ground (FIG. 7), lower guide assembly 110 and sample collection receptacle 104 are supported by the ground and move upward with respect to upper guide assembly 100 and probe 82. When probe 82 is raised out of the ground (FIG. 8), lower guide assembly 110 with extraction finger 106 and sample collection receptacle 104 remain at ground level, and extraction finger 106 ejects a sample from probe 82 into sample collection receptacle 104.

Figure 7:
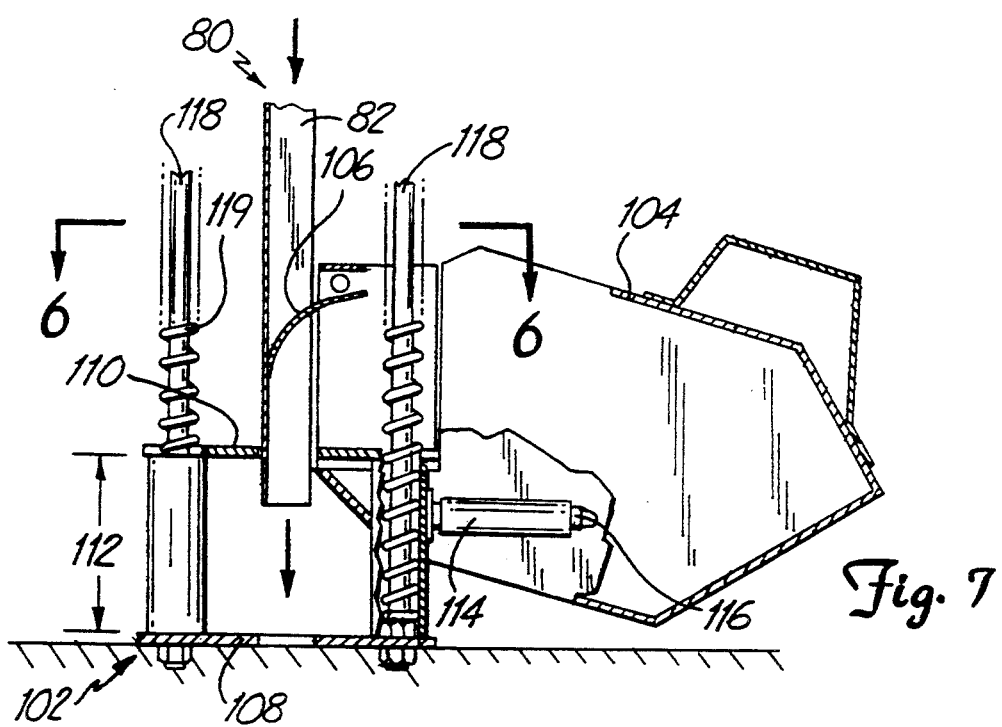
FIG. 7 is an elevational view in partial cross-section of the probe and the sample collection receptacle of the soil sampler, showing the probe and sample collection receptacle prior to pressing the probe into the ground, taken along line 7—7 of FIG. 6.

As shown in FIG. 7, lower guide assembly 102 preferably has a bottom plate 108 and a top plate 110 separated by a distance 112. Placing top plate 110 this distance 112 above bottom plate 108 allows probe 82 to be extracted beyond bottom plate 108, and thus provides for additional room for sample collection receptacle 104 beneath extraction finger 106 without ground interference.

Sample collection receptacle 104 has two sleeves 114 which are sized for mounting on carrier pins 116. No further means to secure sample collection receptacle 104 are provided, and it can be readily removed from lower guide assembly 102 without the use of tools. Slight misalignment between the axes of carrier pins 116 and sleeves 114 may be necessary to provide proper retention of sample collection receptacle 104. Preferably, carrier pins 116 have tapered ends for ease of insertion into sleeves 114. Detachability of sample collection receptacle 104 enhances ease of removing samples from receptacle 104 when the operator so desires. Workers skilled in the art will appreciate that any method of attaching sample collection receptacle 104 to lower guide assembly 102 is suitable so long as it can be readily detached by the operator. Alternatively, sample collection receptacle 104 may be permanently attached to guide 86 if other methods of removing samples are provided.

Figure 6:
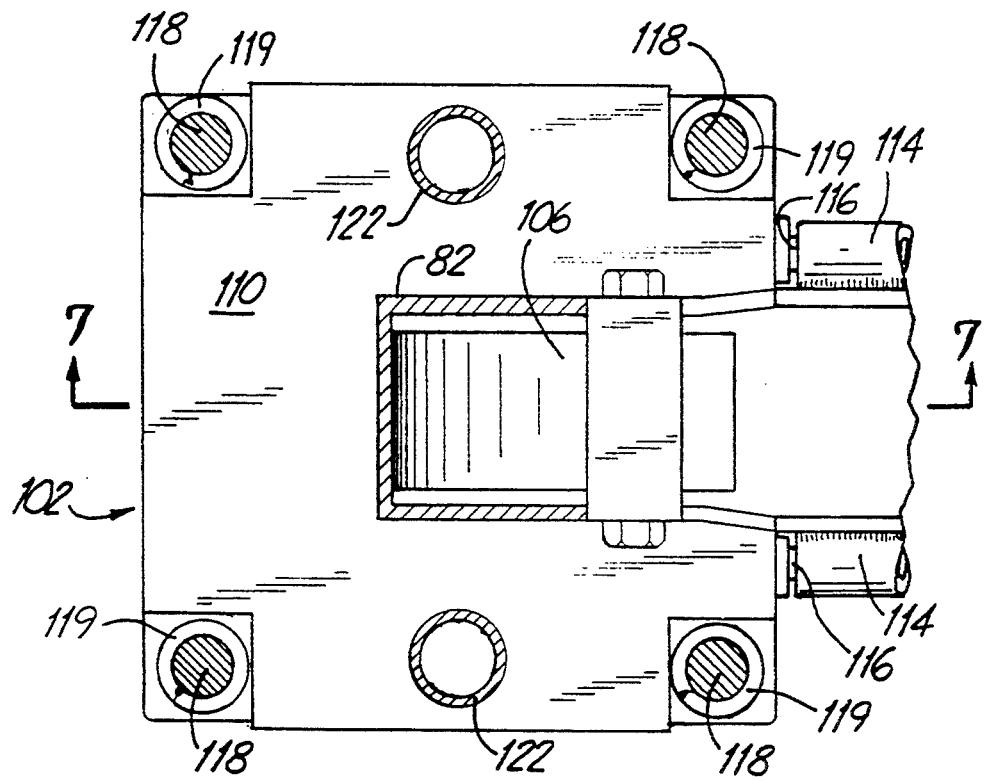
FIG. 6 is a cross-sectional plan view of the probe and the sample collection receptacle of the soil sampler, taken along line 6—6 of FIGS. 1 and 7.

As mentioned above, lower guide assembly 102 is not fixed with respect to probe 82, but rather allows probe 82 to extend through lower guide assembly 102 when probe 82 is inserted into the ground. As shown in FIG. 6, four guide rods 118 are preferably positioned in the corners of lower guide assembly 102. Upper guide assembly 100 has four sleeves 120 (FIG. 5) which slidably receive guide rods 118. Guide rods 118 extend upwardly from lower guide assembly 102 and through sleeves 120. Compression springs 119 may be mounted on guide rods 118.

Upper guide assembly 100 is attached to pins 96 such that it is raised and lowered with probe 82. Sleeves 120 provide a linear bearing surface for upper guide assembly 100 on guide rods 118, to keep probe assembly 80 in alignment when taking samples. When probe 82 is lowered into the ground, upper guide assembly 100 moves downwardly along guide rods 118, while lower guide assembly 102 and sample collection receptacle 104 remain at ground surface, until a full length of probe depth is achieved. Compression springs 119 prevent excessive movement of upper guide assembly 100 into lower guide assembly 102.

As shown in FIG. 6, probe assembly 80 is provided with two depth control tubes 122. Similar to guide rod 118, depth control tubes 122 are attached to lower guide assembly 102 to project upwardly from ground surface through upper guide assembly 100. Each depth control tube 122 includes depth control collar 124 (FIG. 1) which is adjustably located along the length of depth control tube 122. When probe 82 is pressed into the ground, upper guide assembly 100 moves downward, but depth control tubes 122 remain extended above ground level. Contact of upper guide assembly 100 with depth control collars 124 allows for accurately reproducing the insertion depth for probe 82. For maximum probe depth, depth control collars 124 are not used and probe 82 is inserted until upper guide assembly 100 contacts lower guide assembly 102 or compression springs 119 are fully compressed.

Figure 8:
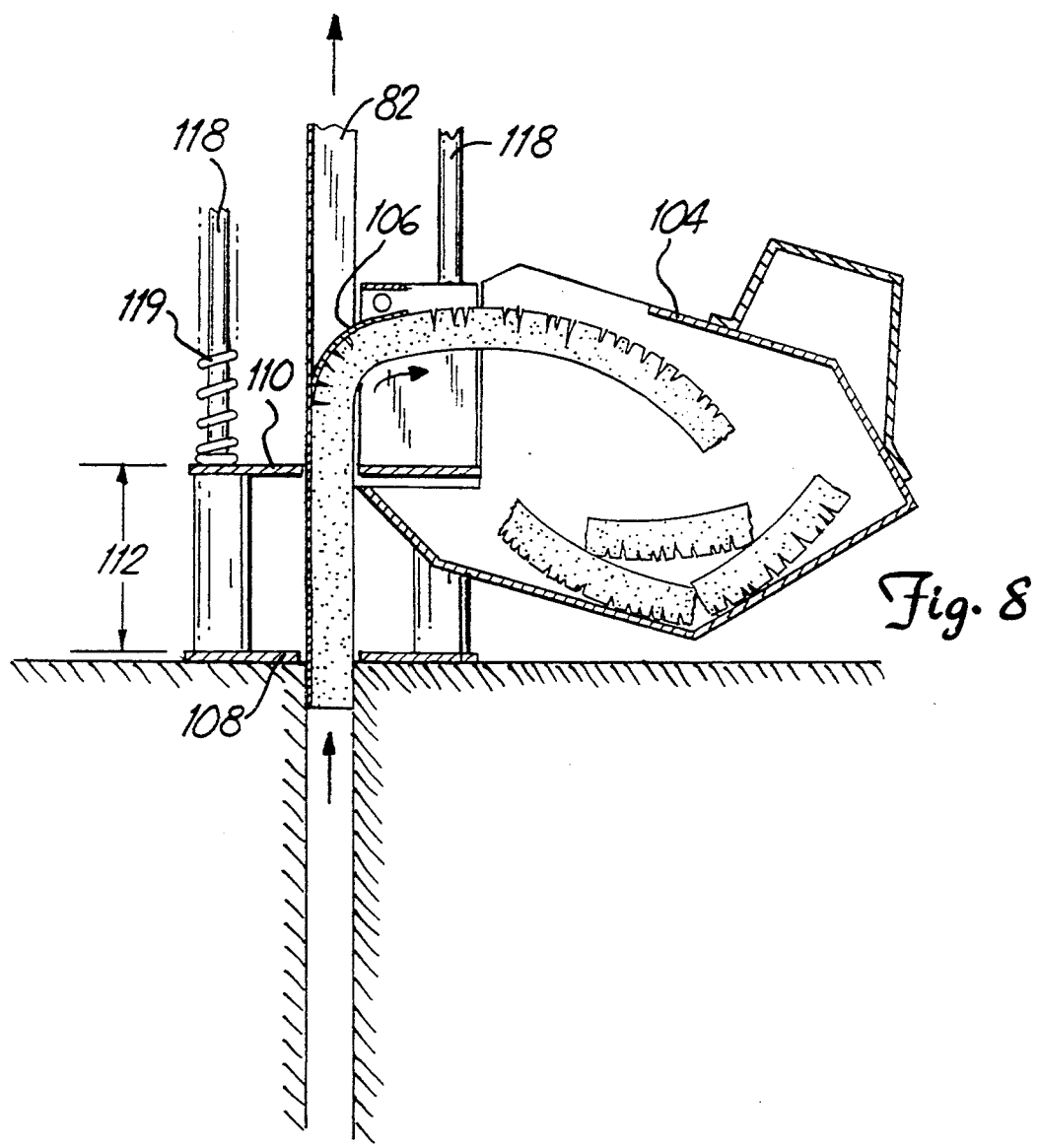
FIG. 8 is the cross-sectional elevational view of FIG. 7, shown during extraction of the probe from the ground.

The operation of probe 82 occurs as follows. When inserted into the ground, the three side walls of probe 82 are pressed around a soil sample. Probe 82 is lowered until upper guide assembly 100 contacts depth control collars 124. As shown in FIG. 8, when probe 82 is raised, extraction finger 106 ejects soil within probe 82 into sample collection receptacle 104. Sample collection receptacle 104 is sized to receive multiple soil samples, such as from five locations of a star-pattern described earlier.

Figure 9:
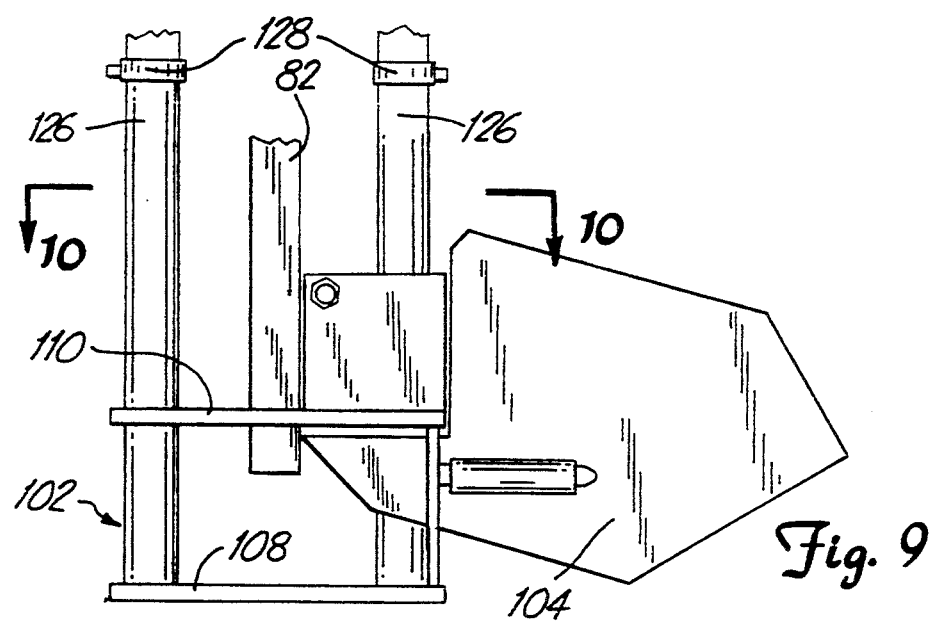
FIG. 9 is an elevational view similar to FIG. 7 of an alternate embodiment of the probe assembly.
Figure 10:
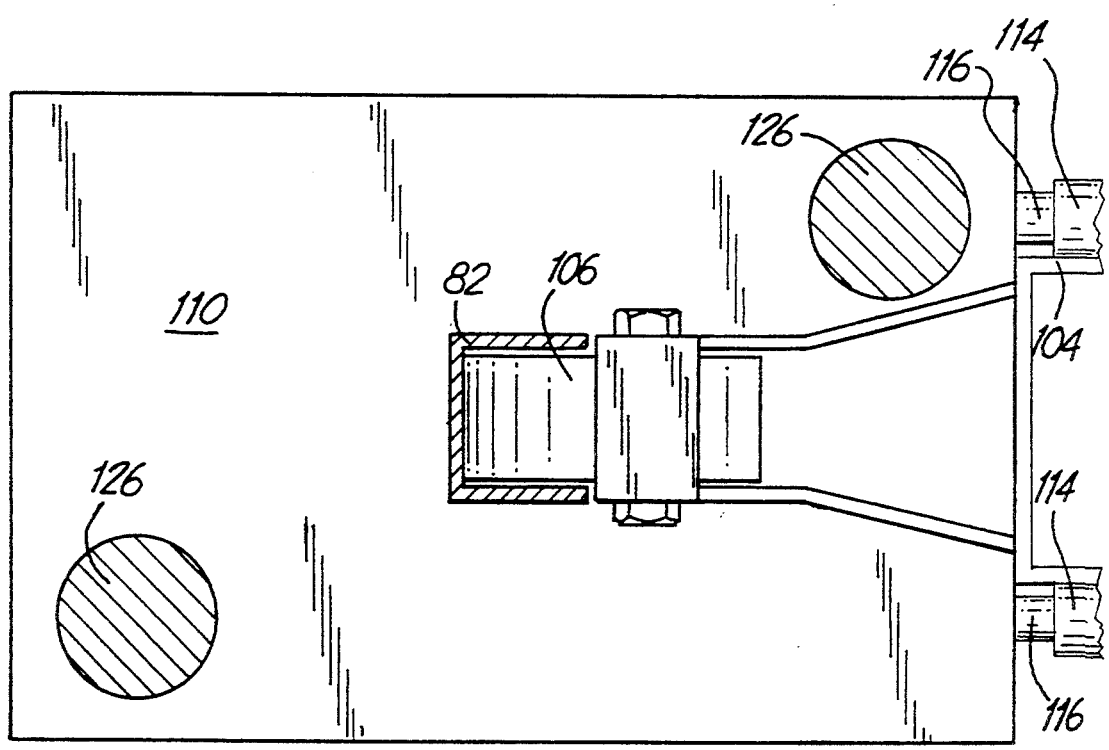
FIG. 10 is a cross-sectional plan view of the alternate embodiment of the probe assembly taken along line 10—10 of FIG. 9.

In an alternate embodiment shown in FIGS. 9 and 10, the four guide rods 118 and two depth control tubes 122 are replaced by two larger combination rods 126. Combination rods 126 have depth stop collars 128 similar in function to depth control collars 124 described previously. When probe 82 is pressed into the ground, upper guide assembly 100 moves downward, but combination rods 126 remain extended above ground level. Contact of upper guide assembly 100 with depth stop collars 128 prevents further insertion of probe 82. By manufacturing combination rods 126 out of stronger or larger diameter tubing, combination rods 126 provide adequate bearing surface for upper guide assembly 100 without using four additional guide rods 118.

Referring now to FIG. 1, soil sampler 10 of the present invention is shown in a sample removal location. Hydraulic cylinder 32 is shortened such that probe 82 is pressed against the ground. As probe 82 is pressed further downward, vibration assembly 50 is activated if and when the ground provides significant resistance to the lowering probe 82. After taking a first sample, boom assembly 20 may be rotated to take a second sample 5–15 feet from the first location. Sample collection receptacle 104 is size to accommodate at least five samples, such that an entire star pattern may be taken without removing the samples.

Referring now to FIG. 3, soil sampler 10 is shown in a position where sample collection receptacle 104 may be removed by an operator without the operator leaving the cab 158 of the vehicle. Hydraulic cylinder 32 is extended such that the lower end of probe assembly 80 is adjacent the driver's window 156 of the pickup 150. The driver may simply reach out of his window, remove sample collection receptacle 104 from carrier pins 116, take the samples from sample collection receptacle 104 and place them into a storage bin or other suitable container for labeling and subsequent handling, and then return sample collection receptacle 104 to carrier pins 116. With this method, soil sampler 10 is ready to take additional samples without any further involvement of the operator.

As shown in FIG. 1, all or part of control panel 130 may be mounted on an umbilical cord 132 and hand control 134 which may be extended into the cab 158 of the pickup truck 150. In this way, the operator can control soil sampler 10 with ever having to leave the cab 158. This is particularly helpful when taking samples from numerous locations around the truck 150 and from numerous truck locations, particularly in inclement weather. Alternatively, control panel 130 could be mounted anywhere desired to provide beneficial access of the operator.

Rotation and raising and lowering of boom assembly 20 can be controlled by the operator such that soil samples are taken from a star-pattern or other desired locations along an arc around the pickup truck 150. Alternatively, movement of boom assembly 20 may be controlled by computer or similar apparatus (not shown) such that a desired sample location pattern is always maintained. Additionally, the computer would be able to reproducibly position probe 82 in the raised location adjacent the driver's window 156 for ease of removing sample collection receptacle 104.

Figure 11:
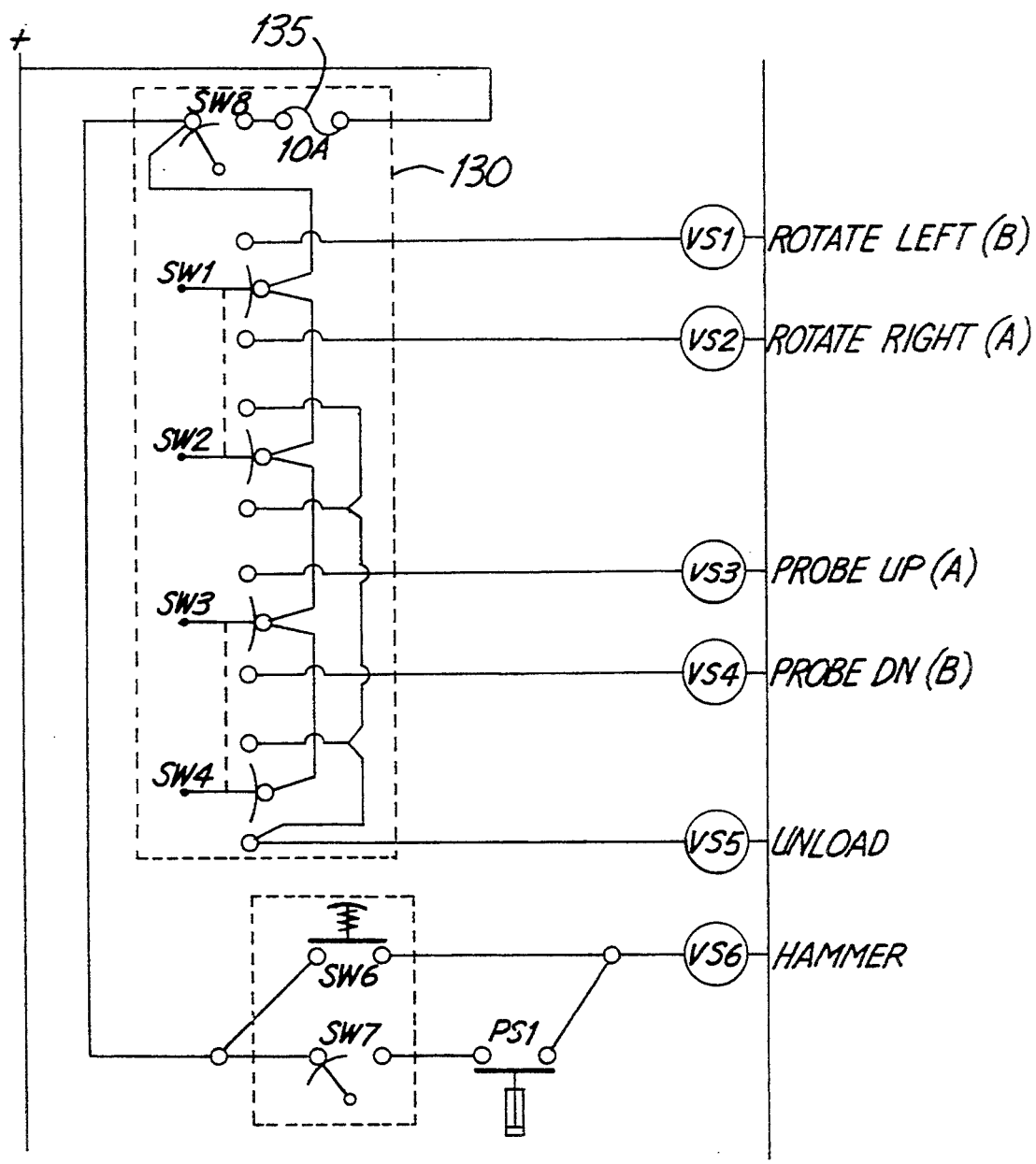
FIG. 11 is an electrical schematic of the soil sampler of the present invention.
Figure 12:
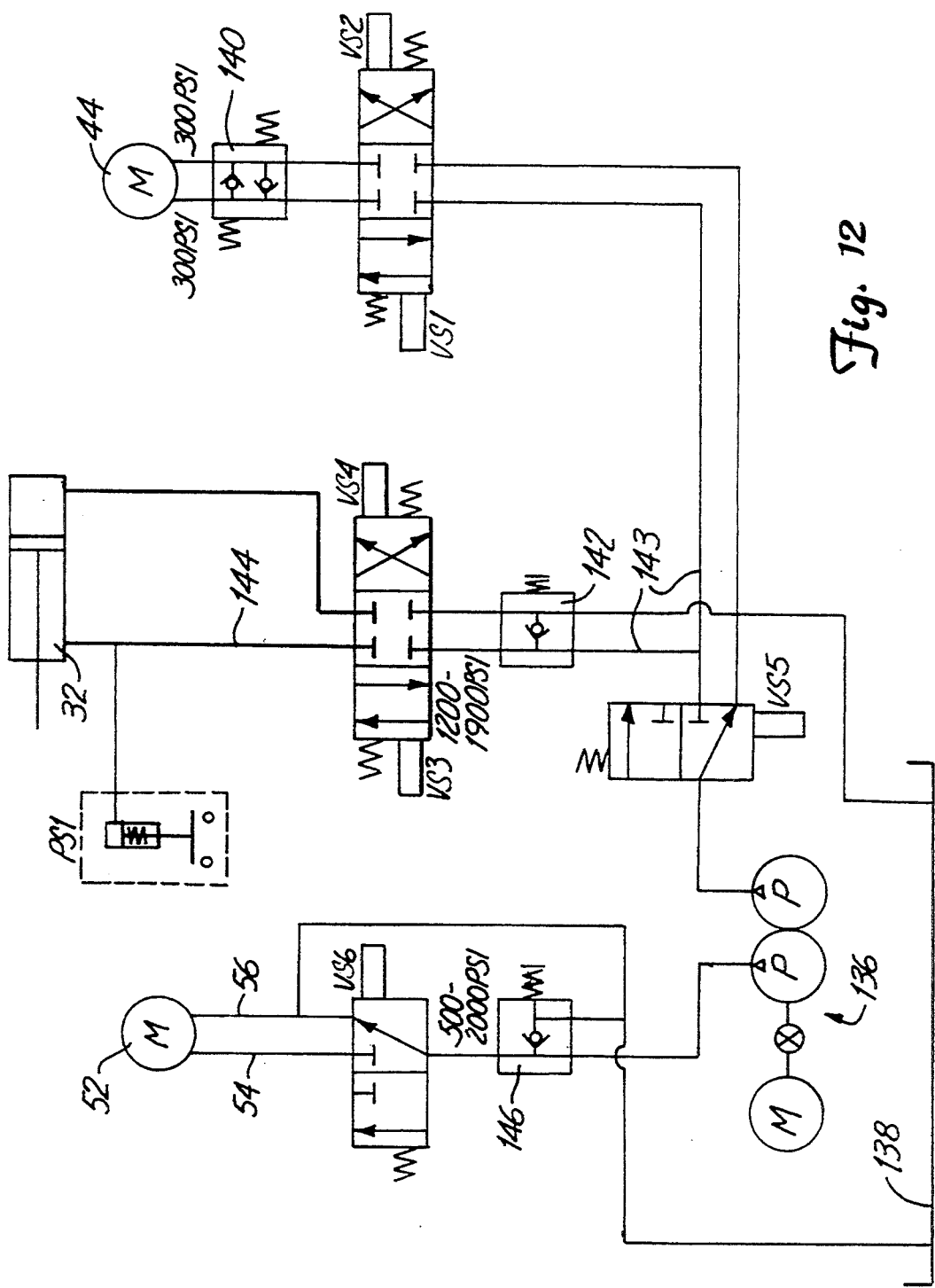
FIG. 12 is a hydraulic schematic of the soil sampler of the present invention.

FIG. 11 shows an electrical schematic for soil sampler 10, and FIG. 12 shows a hydraulic schematic for soil sampler 10. These two schematics read in conjunction detail the operation of the entire preferred system. As shown in FIG. 11, electrical control for soil sampler 10 generally includes eight switches (labelled SW1, SW2, SW3, SW4, SW6, SW7, SW8 and PS1), five of which are external switches operated by the user. Switch SW8, together with 10 amp fuse 135, is a user-operated power switch for the entire system. Switch SW1 is a user-operated toggle switch (which automatically operates switch SW2) for right and/or left rotation of boom assembly 20. Switch SW3 is a user-operated toggle switch (which automatically operates switch SW4) to raise and lower hydraulic cylinder 32.

Switches SW6, SW7 and pressure switch PS1 control vibrator assembly 50. Pressure switch PS1, shown on the hydraulic schematic of FIG. 12, is automatically operated by the hydraulic pressure used to lower boom assembly 20 and normally activates vibrator assembly 50. Switch SW7 is a user-operated, normally-closed toggle switch which allows the user to deactivate vibrator assembly 50 if necessary. User-operated override push-button switch 6 is provided to allow the user to activate vibrator assembly 50 even though the pressure required to activate pressure switch PS1 has not been reached. The various switches activate valve solenoids (VS1 to VS6) as shown in the hydraulic schematic of FIG. 12.

The hydraulic system schematically shown in FIG. 12 is operated off a dual pump 136. An SMP 2 tandem 0.24/0.24 cubic inch motor/pump from Sundstrand Corp. of Rockford, Ill. has been found adequate for this application. Dual pump 136 pressurizes two separate hydraulic circuits, one for the movement of boom assembly 20 and one for vibrator assembly 50.

The hydraulic circuit for movement of boom assembly 20 works as follows. "Unload" valve solenoid VS5 normally directs high hydraulic pressure from dual pump 136 back to hydraulic supply tank 138. However, as the electric schematic of FIG. 11 shows, activation of switch SW1 (for base motor 44) or switch SW3 (for hydraulic cylinder 32) activates valve solenoid VS5 to provide high pressure hydraulic fluid to hydraulic feed lines 143. Base motor 44 (for rotation of boom assembly 20) is activated by valve solenoid VS1 (right rotation) or valve solenoid VS2 (left rotation) through switch SW1. Hydraulic cylinder 32 (for raising/lowering boom assembly 20) is activated through switch SW3, in the up direction by energizing valve solenoid VS3 and in the down direction by energizing valve solenoid VS4.

The hydraulic circuit for base motor 44 includes crossover relief valve 140 setting maximum right and left rotation pressure. A maximum rotation pressure of 300 psi has proven effective to prevent superfluous force on the boom rotation. If boom assembly 20 encounters a fixed object during rotation, then 300 psi maximum pressure will be reached, and crossover relief valve 140 will activate to relieve further pressure. The fixed object could be probe 82 being left inserted in the ground, a wall, a vehicle or even a person. In this way, the system avoids the harmful effects of boom rotation through the object. Crossover relief valve 142 for hydraulic cylinder 32 is provided such that the maximum vertical pressure on the hydraulic system is 1200 to 1900 psi.

Pressure switch PS1 is located on hydraulic feed line 144 to lower boom assembly 20. If the pressure lowering boom assembly 20 exceeds a set pressure (e.g., 200 p.s.i., or any other set pressure appropriate for the application), pressure switch PS1 energizes valve solenoid VS6 and turns on vibrator assembly 50. As can be seen, pressure switch PSI will normally only be activated when probe 82 is meeting significant resistance to being pressed downward into the ground.

Vibrator assembly 50 operates off the second output 54 of dual pump 136 and is activated by valve solenoid VS6. Pressure relief valve 146 is provided such that vibrator assembly 50 works off 500 to 2000 psi hydraulic pressure.

Although the present invention has been described with reference to preferred embodiments, workers skilled in the art will recognize that changes may be made in form and detail without departing from the spirit and scope of the invention.

What is claimed is:

1. A soil sampler comprising:
    a probe to withdraw a soil sample from the ground; and
    a support structure for the probe, the support structure having a base, the support structure being capable of moving the probe to multiple withdrawal locations without moving the base, the support structure being adapted for mounting on a vehicle, movement of the support structure being controllable by an operator within the vehicle, wherein the support structure is capable of raising a soil sample to present the soil sample to the operator within the vehicle and the multiple withdrawal locations are not necessarily in a single vertical plane.

2. The soil sampler of claim 1 further comprising:
    a sample collection receptacle supported by the support structure and positioned adjacent the probe for receiving soil samples.

3. The soil sampler of claim 2 wherein the sample collection receptacle is capable of carrying multiple samples.

4. The soil sampler of claim 2 wherein the sample collection receptacle is readily detachable from the support structure.

5. The soil sampler of claim 2 wherein the support structure is raisable to support the sample collection receptacle adjacent a driver's window of the vehicle.

6. The soil sampler of claim 5 further comprising:
    means for automatically moving the support structure to a position such that the sample collection receptacle is supported adjacent a driver's window of the vehicle.

7. The soil sampler of claim 1 wherein the probe is pivotable with respect to the support structure.

8. The soil sampler of claim 1 further comprising:
    means for inserting the probe into the ground; and
    a depth control to stop insertion of the probe when the probe reaches a desired depth.

9. The soil sampler of claim 1 wherein the support structure is rotatable to locate the probe through 280° of rotation between potential withdrawal locations.

10. The soil sampler of claim 1 wherein the support structure is extendable to locate a lower end of the probe as high as the base.

11. The soil sampler of claim 1 wherein the support structure is hydraulically powered.

12. The soil sampler of claim 1 further comprising:
    means for automatically moving the support structure such that the probe withdraws soil samples from multiple pre-determined withdrawal locations about the vehicle.

13. The soil sampler of claim 1, wherein the support structure is capable of moving the probe through two degrees of freedom.

14. A method of taking a soil sample with a soil sampler, the soil sampler having a supported, moveable probe, the method comprising:
    moving the probe to a first soil withdrawal location;
    inserting the probe into the ground;
    withdrawing a soil sample within the probe from the ground; and
    moving the probe to a second soil withdrawal location without moving the soil sampler and prior to removing the soil sample from the soil sampler wherein the first soil withdrawal location and the second soil withdrawal location are not necessarily in a single vertical plane.

15. The method of claim 14, further comprising the steps of:
    moving the probe to a location adjacent an operator in a vehicle; and
    withdrawing the soil sample from the probe from within the vehicle.

16. The method of claim 15, further comprising the step of:
    having an operator within the vehicle remove the sample collection receptacle from the probe.

17. The method of claim 14, wherein the step of inserting the probe into the ground comprises:
    vibrating the probe.

18. The method of claim 17, wherein the step of vibrating the probe comprises:
    repeatedly hammering the probe with a percussion vibrator.

19. A soil sampler comprising:
    a probe to withdraw a soil sample from the ground;
    a support structure for the probe, the support structure having a base, the support structure being capable of moving the probe to multiple withdrawal locations not necessarily in a single vertical plane without moving the base, the support structure being adapted for mounting on a vehicle; and
    a vibrator to assist in inserting the probe into the ground.

20. The soil sampler of claim 19 wherein the vibrator comprises:
    a motor;
    a vibration unit which vibrates when powered by the motor; and
    a drive shaft to transmit power from the motor to the vibration unit, the drive shaft having a joint which assists in dampening vibration such that the motor is separated from the vibration unit.

21. The soil sampler of claim 20 wherein the vibration unit comprises:
    eccentric weights which cause vibration in a single direction.

22. The soil sampler of claim 18 wherein the vibrator comprises:
    a switch which automatically activates the vibrator when the support structure encounters resistance in moving the probe.

23. The soil sampler of claim 22 wherein the support structure further comprises:
    a hydraulic line for moving the support structure, wherein the switch is activated off the pressure of the hydraulic line.

24. The soil sampler of claim 19 wherein the vibrator comprises: a hammer to vibrate the probe.

25. The method of claim 14, further comprising the step of:
    ejecting the soil sample from the probe into a sample collection receptacle.

* * * * *

UNITED STATES PATENT AND TRADEMARK OFFICE
CERTIFICATE OF CORRECTION

PATENT NO. : 5,435,399

DATED : July 25, 1995

INVENTOR(S) : GARY G. PETERSON; JACOB N. GUST; VIRGIL R. MAHLUM; MICHAEL W. SMETTE

It is certified that error appears in the above-indentified patent and that said Letters Patent is hereby corrected as shown below:

Col. 1, line 15, before "crops", delete "."

Signed and Sealed this

Twenty-third Day of April, 1996

Attest:

BRUCE LEHMAN

Attesting Officer

Commissioner of Patents and Trademarks